United States Patent
Jadhav et al.

(10) Patent No.: US 12,268,837 B2
(45) Date of Patent: Apr. 8, 2025

(54) NEUTRAL DISPLACEMENT CONNECTOR

(71) Applicant: CareFusion 303, Inc., San Diego, CA (US)

(72) Inventors: Amarsinh Deeliprao Jadhav, Bangalore (IN); Sumit Rajpal, Panipat (IN); Abin Austin, Thrissur (IN); Kaushik Suman, Bengaluru (IN); Kanjimpuredathil Muralikrishna Menon, Bangalore (IN)

(73) Assignee: CAREFUSION 303, INC., San Diego, CA (US)

( * ) Notice: Subject to any disclaimer, the term of this patent is extended or adjusted under 35 U.S.C. 154(b) by 7 days.

(21) Appl. No.: 18/090,234

(22) Filed: Dec. 28, 2022

(65) Prior Publication Data

US 2024/0216668 A1 Jul. 4, 2024

(51) Int. Cl.
*A61M 39/26* (2006.01)
*A61M 39/10* (2006.01)

(52) U.S. Cl.
CPC ............ *A61M 39/26* (2013.01); *A61M 39/10* (2013.01); *A61M 2039/1027* (2013.01); *A61M 2039/263* (2013.01); *A61M 2039/266* (2013.01)

(58) Field of Classification Search
CPC ............ A61M 39/26; A61M 2039/262; A61M 2039/263; A61M 2039/266; A61M 39/10; A61M 2039/1027; A61M 2039/2433
See application file for complete search history.

(56) References Cited

U.S. PATENT DOCUMENTS 5,569,235 A * 10/1996 Ross ..................... A61M 39/26
 604/249
5,782,816 A * 7/1998 Werschmidt .......... A61M 39/02
 251/149.6
6,029,946 A 2/2000 Doyle
(Continued)

OTHER PUBLICATIONS

Fanninhealthcare, "MircroClave Clear Neutral Displacement Connector", YouTube, 2012, https://www.youtube.com/watch?v=yM27WuV2IKU.

(Continued)

*Primary Examiner* — David Colon-Morales
(74) *Attorney, Agent, or Firm* — Morgan, Lewis & Bockius LLP

(57) ABSTRACT

Fluid connectors assemblies that provide neutral fluid displacement without overlapping connectors are disclosed. A fluid connector assembly may include a housing and a pair of connectors (e.g., luers) coupled with the housing. A compressible member is located within the housing. The first connector and the second connector each include a post with an opening. The compressible member can seal off the opening of the first connector from fluid entry. However, when the post of the second connector is inserted into the housing, the post of the second connector displaces the compressible member, causing the compressible member to create a fluid path, thereby allowing fluid to flow through the internal volume of the housing. Further, the compressible member seals the housing until each of the first connector and the second connector are coupled therewith forming a fluid path through the posts.

18 Claims, 8 Drawing Sheets

(56) References Cited

U.S. PATENT DOCUMENTS

| | | | |
|---|---|---|---|
| 8,511,638 B2* | 8/2013 | Mansour | A61M 39/26 251/149.6 |
| 8,708,976 B1* | 4/2014 | Yeh | A61M 39/26 604/236 |
| 8,801,678 B2* | 8/2014 | Panian | F16J 1/01 604/905 |
| 9,067,049 B2* | 6/2015 | Panian | A61M 39/10 |
| 9,144,672 B2* | 9/2015 | Mansour | A61M 39/10 |
| 9,278,205 B2* | 3/2016 | Quach | A61M 39/10 |
| 9,370,651 B2* | 6/2016 | Zollinger | A61M 39/22 |
| 9,375,561 B2* | 6/2016 | Mansour | A61M 39/10 |
| 9,440,060 B2 | 9/2016 | Fangrow | |
| 9,750,926 B2 | 9/2017 | Lopez et al. | |
| 11,116,958 B2* | 9/2021 | Ueda | A61M 39/26 |
| 11,389,635 B2* | 7/2022 | Mason | A61M 39/26 |
| 2011/0130724 A1 | 6/2011 | Mansour et al. | |
| 2013/0030386 A1 | 1/2013 | Panian et al. | |
| 2014/0276459 A1* | 9/2014 | Yeh | A61M 39/26 604/256 |
| 2017/0014618 A1* | 1/2017 | Ueda | A61M 39/26 |
| 2023/0277835 A1* | 9/2023 | Akiyama | A61M 39/24 251/149.7 |

OTHER PUBLICATIONS

International Search Report and Written Opinion for Application No. PCT/US2023/085750, dated Apr. 26, 2024, 11 pages.

* cited by examiner

NEUTRAL DISPLACEMENT CONNECTOR

TECHNICAL FIELD

The present disclosure relates generally to medical fluid connectors and, more particularly, to neutral displacement needle-free connectors that utilize a deformable member to control fluid flow.

BACKGROUND

Needle-free connectors, including neutral displacement needle-free connectors, offer a solution for providing medical fluid to patients. In an exemplary embodiment, a needle-free connector assembly promotes fluid transmission between a medical fluid supply and a catheter line. The medical fluid supply and the catheter line are secured to respective luers that are secured to a connector body. To transmit fluid, the luer connected to the medical supply is inserted into the connector body and overlaps a central post of the luer connected to the catheter line.

The overlapping between the luer and the central post can lead to issues. For example, movement of the luer relative to the central post, or vice versa, can cause contact between the luer and the central post, leading to increased risk of cracking or breaking the central post. When this occurs, the damaged area leads to fluid leakage, resulting in fluid loss and contamination. Additionally, luers used with neutral displacement connectors are often non-compliant luers, making them susceptible to fluid leakage.

SUMMARY

In accordance with at least some embodiments disclosed herein is the realization that components used with neutral fluid displacement, such as a luer and a post, can break when overlapping and coming into contact with each other, which can result in medical fluid leakage and reduced medical delivery to a patient. When a broken component is located in a connector body, it may not be readily present to a medical professional that the component is broken, leading to delayed response times.

Aspects of the present disclosure provide a needle-free fluid connector assembly that provides a neutral fluid displacement connection while eliminating the risk of breaking one or more components of the needle-free fluid connector assembly. The neutral fluid displacement limits or prevents fluid from entering a catheter lumen during connection or disconnection of a medical fluid.

Accordingly, aspects of the present disclosure provide a fluid connector assembly comprising a housing comprising a first end in fluid communication with a second end through a cavity, a compressible member disposed within the housing, the compressible member comprising at least one sealing element; and a gate, a first connector configured to couple to the housing at the first end, the first connector configured to deliver a fluid through the housing; and a second connector configured to couple to the housing at the second end, the second connector configured to receive a fluid from the housing.

Some instances of the present disclosure provide a fluid connector assembly comprising a housing comprising a first end in fluid communication with a second end through a cavity, a compressible member disposed within the housing, the compressible member comprising at least one sealing element; and a gate, a first connector configured to couple to the housing at the first end, the first connector configured to deliver a fluid through the housing; and a second connector configured to couple to the housing at the second end, the second connector configured to receive a fluid from the housing; wherein the compressible member is configured to deform from an expanded configuration to a compressed configuration when the first connector is coupled to the housing; and wherein the compressible member is configured to deform substantially to a first side of the cavity in the compressed configuration.

Accordingly, the present application addresses several operational challenges encountered in prior neutral displacement connector assemblies that are susceptible to breaking.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures.

DETAILED DESCRIPTION

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present disclosure may be disclosed or shown in the context of an intravenous ("IV") set, such embodiments can be used in other fluid conveyance systems. Furthermore, various applications of such embodiments and modifications thereto, which may occur to those who are skilled in the art, are also encompassed by the general concepts described herein.

In accordance with some embodiments, the present disclosure includes various features and advantages of maintaining separation between a post and luer, thus minimizing the likelihood of damaging the post and/or the luer.

Figure 1:
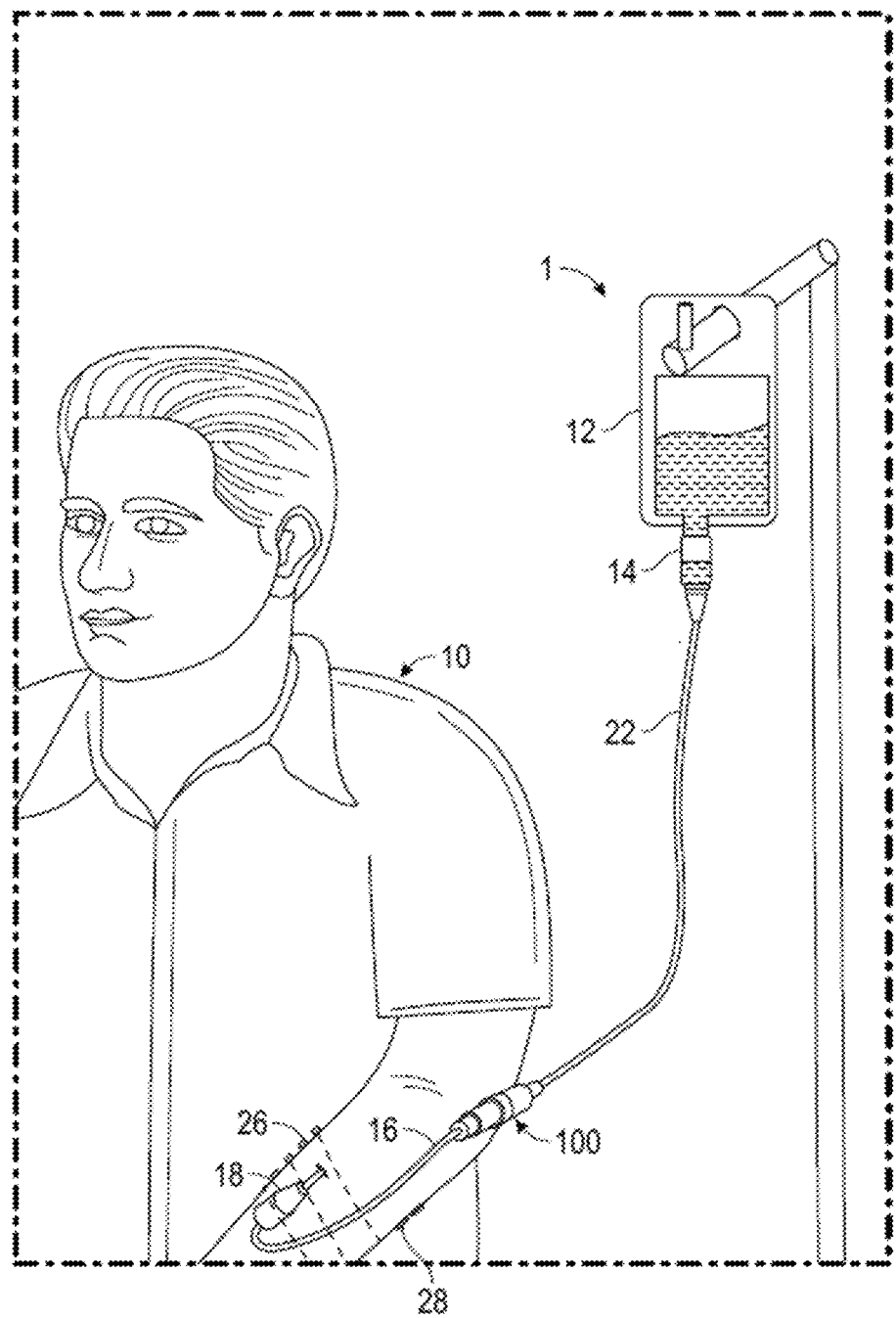
FIG. 1 illustrates an IV set coupled to a patient, in accordance with aspects of the present disclosure.

Referring now to the figures, FIG. 1 illustrates an IV set 1 coupled to a patient 10, in accordance with aspects of the present disclosure. The IV set 1 includes a medicament bag 12, a drip chamber 14, and tubing 22. The tubing 22 extends between the drip chamber 14 and a fluid connector assembly 100 of the IV set 1. To resist unintended dislodgement or disconnection of the tubing 16 or the catheter 18 from the patient, tape 26 is placed over the tubing 16 and the catheter 18, so that the tape 26 engages the tubing 16, the catheter 18, and the patient 10.

Figure 2:
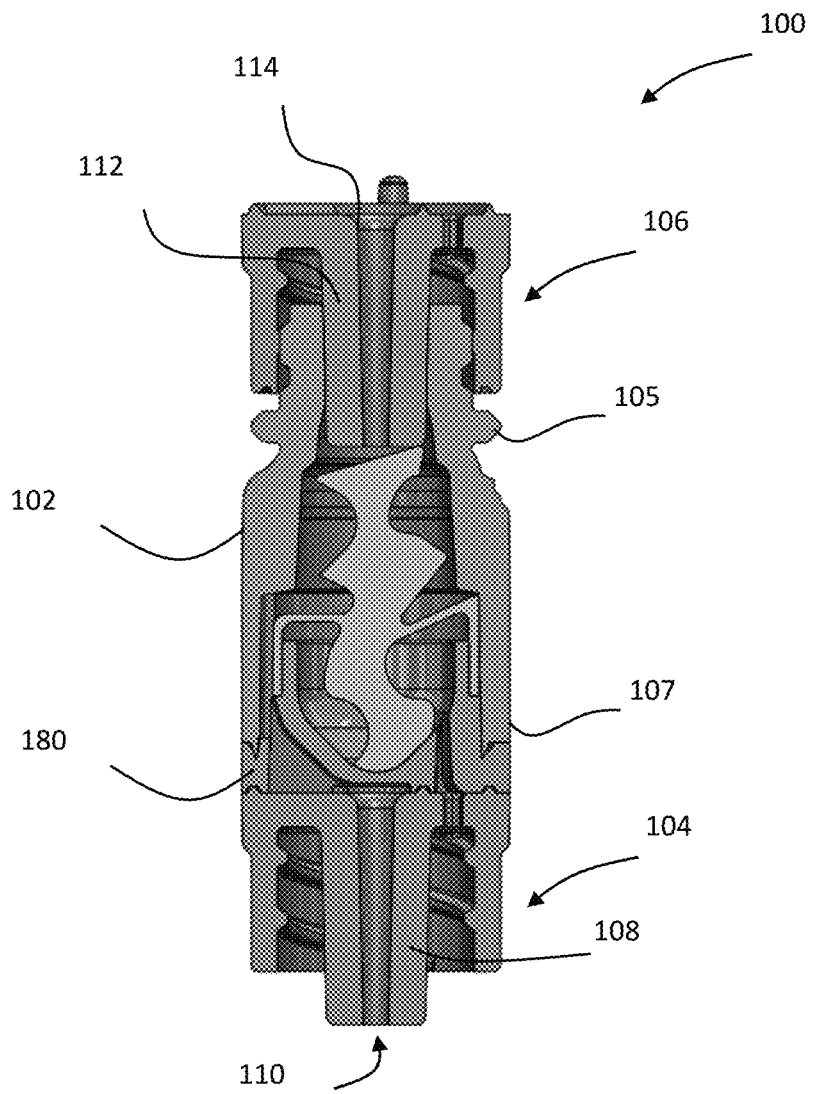
FIG. 2 illustrates a perspective view of a fluid connector assembly for in use with an IV set, in accordance with aspects of the present disclosure.

FIG. 2 illustrates a perspective view of a fluid connector assembly 100 for use with an IV set, in accordance with aspects of the present disclosure. The fluid connector assembly 100 is designed for use in medical applications, such as the IV set 1 (shown in FIG. 1) as well as other IV medical fluid delivery applications using catheters, including peripheral intravenous catheters ("PIVC"), as non-limiting examples.

The fluid connector assembly 100 provides a regulated fluid path throughout the components of the fluid connector assembly 100. As shown, the fluid connector assembly 100 includes a housing 102 used as a central body to carry and/or connect with one or more components. The housing 102 may include a cylindrical, or generally cylindrical, body. Additionally, the housing 102 may include a hollow, or generally hollow, body that forms an internal volume to receive one or more components. In some embodiments, the housing 102 is made of a polycarbonate, polycarbonate acrylonitrile butadiene styrene blend, or another material such as a plastic or a metal.

The fluid connector assembly 100 further includes connector 104 and a connector 106, each of which can couple, including mechanically couple, with the housing 102. As shown, the housing 102 includes an end 105 and an end 107, and the connector 104 and the connector 106 is connected to the end 105 and the end 107, respectively. The connectors 104 and 106 may be referred to as a first connector and a second connector, respectively. Also, the end 105 and the end 107 may be referred to as a first end and a second end, respectively. However, "first" and "second" may be interchangeable for the connectors 104 and the 106, as well as the ends 105 and 107. Also, each of the connectors 104 and 106 may be referred to as a medical connector. In some embodiments, the connector 106 is connected to a medical fluid, such as the medicament bag 12 (shown in FIG. 1). Further, in some embodiments, the connector 104 is connected to a catheter line (e.g., tubing 16 in FIG. 1) that delivers the medical fluid to a catheter, such as the catheter 18 (shown in FIG. 1). Also, each of the connectors 104 and 106 may take the form of a luer designed to prevent fluid leakage through their respective connections with the housing 102. In this regard, each of the connectors 104 and 106 may conform to standards established by the International Organization for Standards ("ISO") to improve patient safety, minimize medical fluid leakage, and reduce misconnection with other connection devices. In some embodiments, each of the connectors 104 and 106 may not conform to standards established by the ISO. In some embodiments, the connectors 104 and 106 are made of a polycarbonate, polycarbonate acrylonitrile butadiene styrene blend, or another material such as a plastic or a metal.

The connector 104 includes a post 108 that includes a channel fluidly connected to an opening (not shown in FIG. 2) at the end of the post 108. As a result, the fluid outlet 110 acts as a fluid transmission location for the fluid connector assembly 100. Also, the connector 106 includes a post 112 that includes an opening 114. The opening 114 acts as a fluid inlet of the fluid connector assembly 100. Accordingly, the opening 114 acts as a fluid receiving location for the fluid connector assembly 100. Each of the posts 108 and 112 can pass centrally, or at least approximately centrally, through the connectors 104 and 106, respectively. The posts 108 and 112 may be referred to as a first post and a second post, respectively. However, "first" and "second" may be used interchangeably. Also, each of the posts 108 and 112 includes a conical, or generally conical, shape. However, other shapes are possible, including but not limited to cylindrical shaped.

Figure 3:
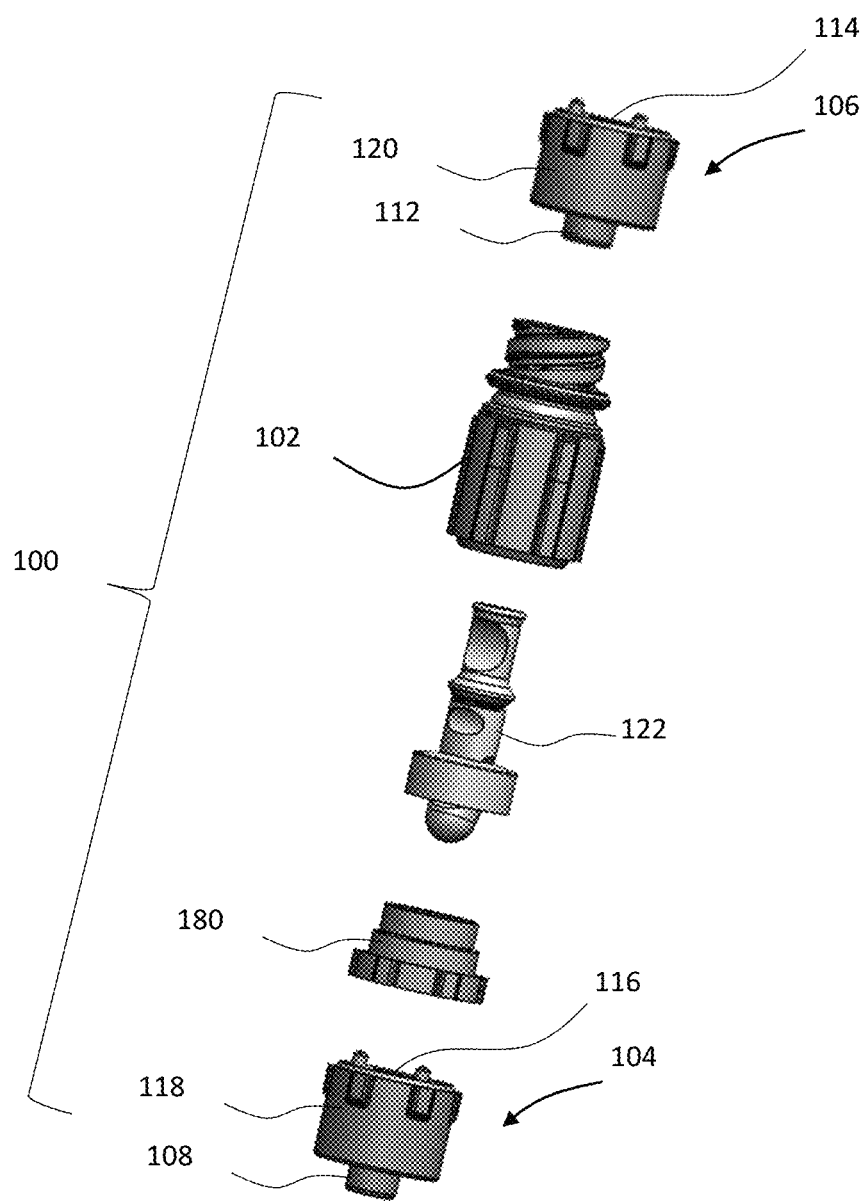
FIG. 3 illustrates an exploded view of the fluid connector assembly, showing additional features, in accordance with aspects of the present disclosure.

FIG. 3 illustrates an exploded view of the fluid connector assembly 100, showing additional features, in accordance with aspects of the present disclosure. The connector 104 includes an opening 116 formed in the post of the connector 104. The opening 116 represents a fluid inlet for the connector 104. The opening 116 is fluidly connected to the fluid outlet 110. Additionally, each of the connectors 104 and 106 include connector portions integrated with the respective posts. For example, the connector 104 includes a connector portion 118 and the connector 106 includes a connector portion 120. As shown in FIG. 3, the posts 108 and 112 extend through the connector portions 118 and 120, respectively. The fluid connector assembly 100 further includes an insert 180. In some embodiments, the insert 180 is located between the connector 104 and the housing 102. In some embodiments, the insert 180 is made of a polycarbonate, polycarbonate acrylonitrile butadiene styrene blend, or another material such as a plastic or a metal. In some embodiments, the connector 104 is welded to the insert 180. In some embodiments, the insert 180 is welded to the housing 102. In some embodiments, the connector 104 is welded to the insert 180 and the housing 102 is welded to the insert 180. In some embodiments, the fluid connector assembly 100 comprises four parts, the connector 104, the insert 180, the housing 102 and the compressible member 122. In some embodiments, the fluid connector assembly 100 comprises less than two parts when the insert 180, the housing 102 and the compressible member 122 are welded together. In some embodiments, the fluid connector assembly 100 comprises less than two parts when the insert 180 and either the housing 102 or the compressible member 122 are welded together.

Additionally, the fluid connector assembly 100 includes a compressible member 122. In some embodiments, the compressible member 122 can elastically compress. Accordingly, the compressible member 122 can compress by an external force (or by multiple external forces) and subsequently return to its original, uncompressed state when the external force is removed. The compressible member 122 is designed to regulate fluid flow through the fluid connector assembly 100. Accordingly, the compressible member 122 acts as a valve for the fluid connector assembly 100. This will be shown in detail below.

Figure 4:
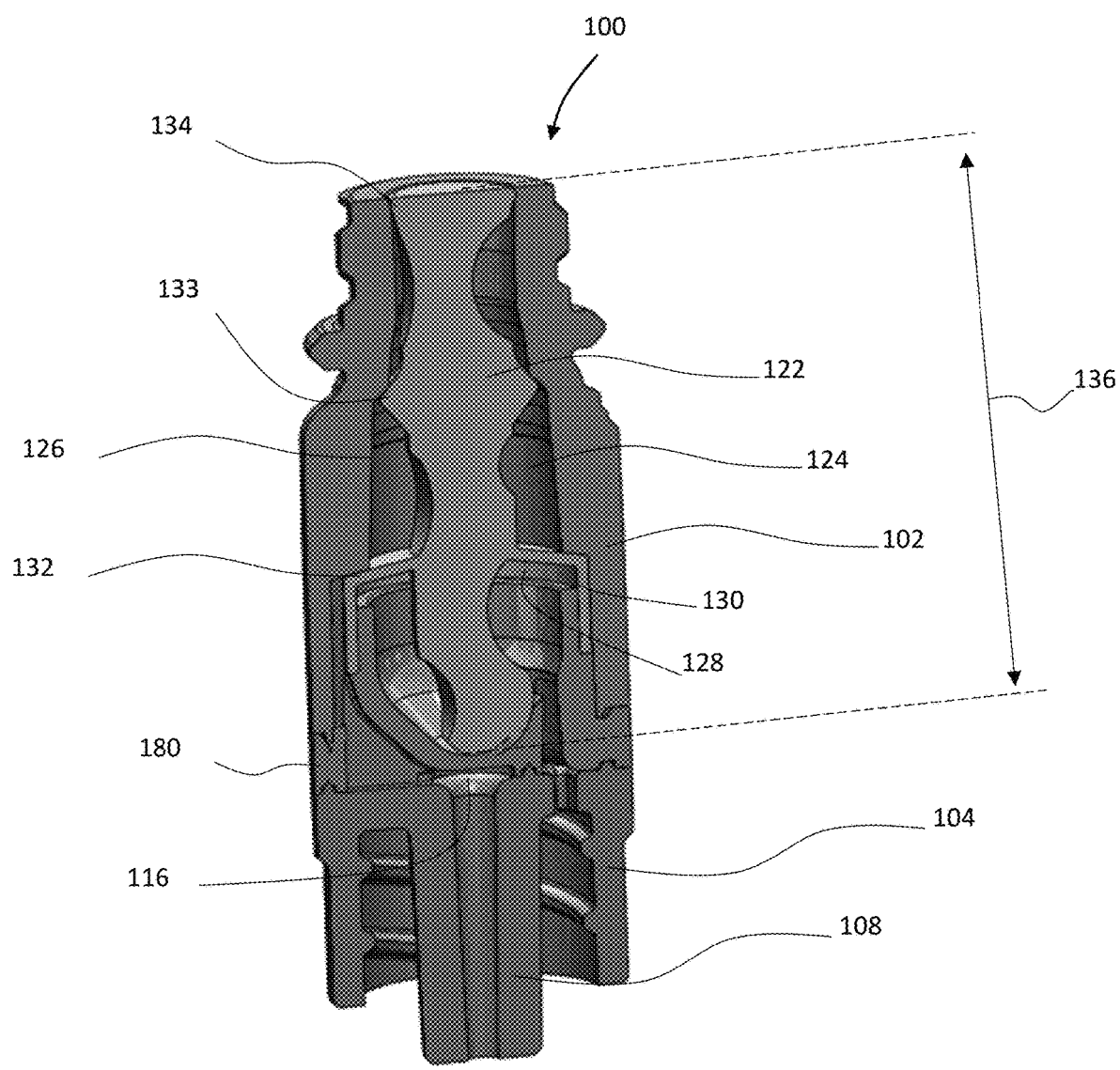
FIG. 4 illustrates a partial cross-sectional view of the fluid connector assembly, showing the first connector, the insert, and the compressible member positioned in the housing, in accordance with aspects of the present disclosure.

FIG. 4 illustrates a partial cross-sectional view of the fluid connector assembly 100, showing the connector 104 and the compressible member 122 positioned in the housing 102, in accordance with aspects of the present disclosure. Based on the hollow design, the housing 102 includes an internal volume 124 that forms a three-dimensional space or void in the housing 102, thus allowing the housing 102 to receive one or more components. For example, the compressible member 122 and a portion of the insert 180 are positioned in the internal volume 124. The housing 102 further includes an inner surface 126, or wall, that at least partially defines the internal volume 124 of the housing 102.

Additionally, a portion of the insert 180 is located in the compressible member 122. In this regard, the compressible member 122 includes an internal volume 128 within a gate 132 through which the portion of the insert 180 lies. The gate 132 of the compressible member 122 further includes an inner surface 130, or wall, that at least partially defines the internal volume 128 of the compressible member 122. In some embodiments, the gate 132 is a septum. In some embodiments, part of the gate is a septum. Also, as shown in FIG. 4, the inner surface 130 of the compressible member 122 surrounds the insert 180. Moreover, the inner surface 130 of the compressible member 122 is in contact with the insert 180. As a result of this relationship between the inner surface 130 and the insert 180, the compressible member 122 prevents fluid flow through the insert 180. In some embodiments, the gate 132 of the compressible member 122 provides a liquid-sealing structure that forms a seal between the insert 180 and the compressible member 122 to prevent fluid leakage between the insert 180 and the compressible member 122. In some embodiments, the gate 132 can be integrated with the compressible member 122, and in some embodiments, the gate 132 may be separated from the compressible member 122. In some embodiments, the compressible member 122 is made of a liquid silicone rubber, or another material such as a plastic.

The compressible member 122 further includes a primary seal 133 and a secondary seal 134 extending circumferentially within the internal volume 124 of the housing 102. As shown in FIG. 4, the primary seal 133 and the secondary seal 134 may resist fluid flow by contacting the inner surface 126 of the housing 102. However, when the connector 106 (shown in FIG. 3) is coupled with the housing 102, the post 112 of the connector 106 can engage the compressible member 122, causing the primary seal 133 and the secondary seal 134 to translate based upon the applied force provided by the post 112.

Further, the compressible member 122 includes a dimension 136 that defines a lengthwise dimension of a major axis of the compressible member 122. When no external force is acting on the compressible member 122 to displace (e.g., compress) the compressible member 122, the lengthwise dimension of the compressible member 122 is defined by the dimension 136. Accordingly, the dimension 136 of the compressible member 122 represents an initial dimension, and the size and shape of the compressible member 122 shown in FIG. 4 represents an initial size and shape.

Figure 5:
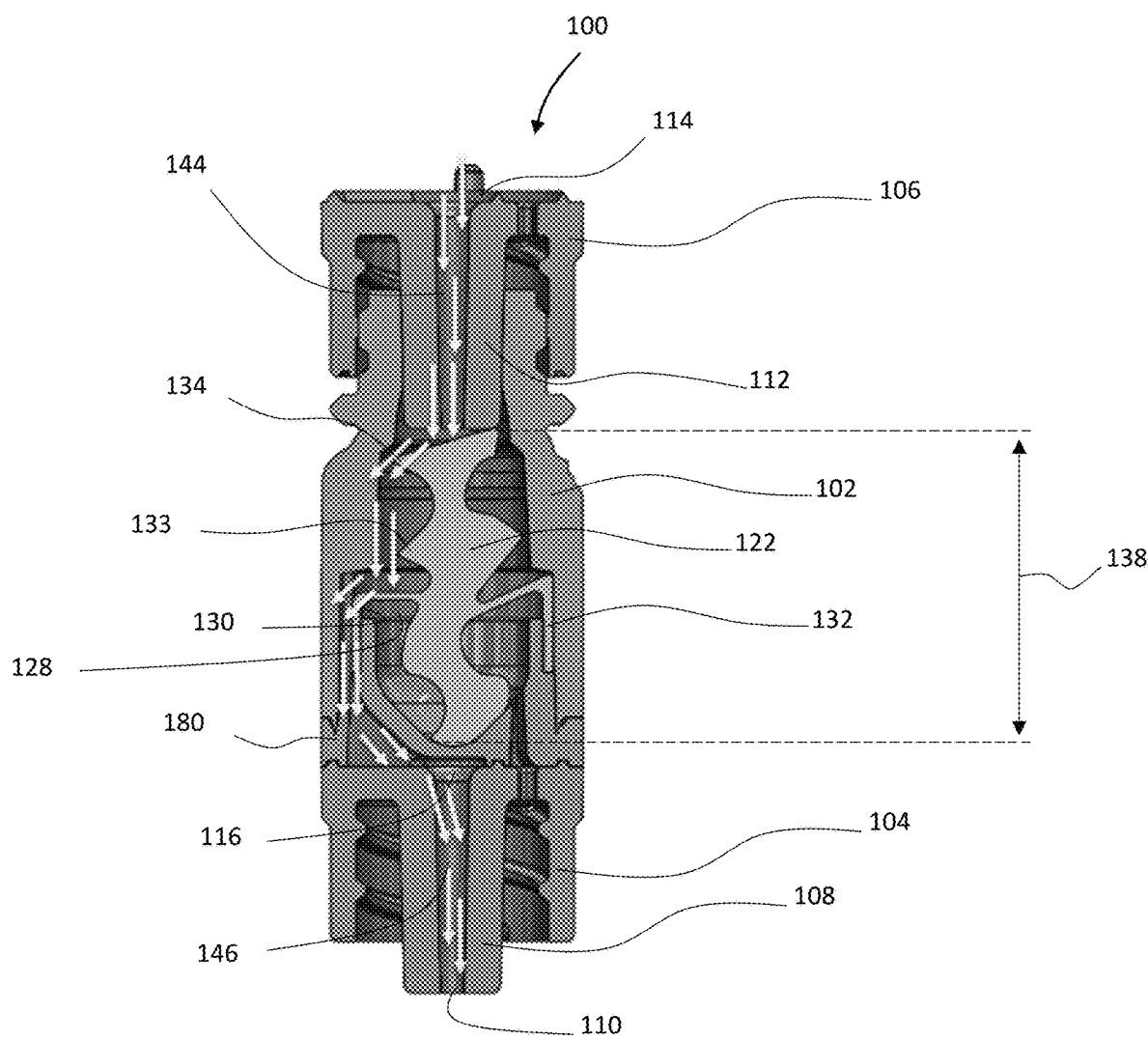
FIG. 5 illustrates a partial cross-sectional view of the fluid connector assembly, showing the first connector, the second connector, the insert, and the compressible member inserted into the housing, in accordance with aspects of the present disclosure.

FIG. 5 illustrates a partial cross-sectional view of the fluid connector assembly 100, showing the connector 106 inserted into the housing 102, in accordance with aspects of the present disclosure. As shown, the post 112 of the connector 106 is at least partially disposed in the housing 102 and engages the compressible member 122, causing the compressible member 122 to displace. For example, the compressible member 122 compresses and reduces to a dimension 138 that is less than the dimension 136 (the original, uncompressed dimension shown in FIG. 4). Based on the displacement of the compressible member 122, each of the internal volume 128 and the inner surface 130 of the compressible member 122 transforms. For example, the internal volume 128 reduces and expands around the insert 180, and the inner surface 130 of the compressible member 122 no longer circumferentially engages the inner surface 126. Further, the displacement of the compressible member 122 causes the primary seal 133 and the secondary seal 134 of the compressible member 122 to separate from the inner surface 126. As a result, fluid passing through the post 112 of the connector 106 can travel through the internal volume 124, past the gate 132, through the insert 180, and further pass through the opening 116 of the post 108. Accordingly, in the displaced configuration of the compressible member 122, the opening 116 of the post 108 is fluidly connected to the primary seal 133 and the secondary seal 134 of the compressible member 122. In some embodiments, when the connector 106 is moved 0.5 mm away from the housing 102 the gate 132 prevents fluid from flowing. In some embodiments, the gate 132 prevents flow when the connector 106 is moved less than 0.5 mm away from the housing 102.

The compressible member 122 is shaped such that the deformation thereof can be highly predictable and repeatable. As such, the compressible member 122 is intended to experience more deformation in the portion between the gate 132 and the connector 106 than portion between the gate 132 and the insert 180 experiences. As shown in FIG. 5, the secondary seal 134 and primary seal 133 both deform axially toward the gate 132 and radially toward the side of the internal volume 124 that the gate 132 is located. The gate 132 is designed to deform axially on one side as well. This deformation allows a fluid path to be created between the compressible member 122 and the inner surface 126. This designed deformation can allow the fluid to reach a target outlet of the housing 102, here the gate 132, which directs the fluid through the insert 180 and into the connector 104.

The arrows show a fluid path through the fluid connector assembly 100. When a medical fluid line is connected to the connector 106, the fluid enters the opening 114 (i.e., fluid inlet) of the connector 106. The fluid can then pass through the channel 144 of the post 112 and enter the internal volume 124 of the housing 102. The fluid can then pass through a space between the gate 132 and the inner surface 126 to enter the insert 180. The fluid can then enter the opening 116 of the post 108, and subsequently pass through a channel 146 of the post 108. The fluid can exit the fluid connector assembly 100 through the fluid outlet 110 formed in the post 108.

Upon removal of the connector 106, the compressible member 122 expands and returns to its original shape and size. In this regard, the compressible member 122 returns to having the dimension 136, representing the original lengthwise dimension of the compressible member 122 prior to displacement by the post 112 of the connector 106. Further, the primary seal 133 and the secondary seal moved back into circumferential contact with the inner surface 126 after removal of the connector 106, and the primary seal 133 and the secondary seal 134 prevents fluid passage therethrough. Additionally, the internal volume 128 of the compressible member 122 returns to its prior, uncompressed volume and the gate 132 of the compressible member 122 returns to its position against the inner surface 126 preventing fluid passage therethrough.

Based on the fluid flow through the fluid connector assembly 100, the fluid connector assembly 100 provides neutral fluid displacement in which blood and/or other fluids is/are prevented, or at least substantially limited, from entering a catheter lumen (not shown) positioned in the connector 104 and fluidly connected to the fluid connector assembly 100 during a connector or disconnection between the fluid connector assembly 100 and the catheter lumen, or when the medical fluid line is connected or disconnected to the connector 106. However, unlike traditional neutral fluid displacement connector assemblies, the post 108 of the connector 104 is not inserted into the post 112 of the connector 106. Put another way, the post 112 of the connector 106 does not overlap the post 108 of the connector 104. As shown in FIG. 5, a gap, or separation, exists between the post 108 and the post 112. Accordingly, when the connectors 104 and 106 are coupled with the housing 102, the posts 108 and 112 are separated by the gap in a direction along a longitudinal axis that passes through the housing 102, the connectors 104 and 106, and the compressible member 122.

Despite the gap, the primary seal 133 and the secondary seal 134 promote fluid flow around one side of the compressible member 122. For example, the secondary seal 134 urges fluid exiting the post 112 into a first side of the internal volume 124 and prevents fluid flowing into a second side of the internal volume 124. Also, the primary seal 133 further urges the fluid flowing through the first side of internal volume 124. As a result, fluid entering the fluid connector assembly 100 remains within the connector 106, the internal volume 124, the insert 180, and the connector 104. Based on the features and functionality, the fluid connector assembly 100, unlike positive fluid displacement connector assemblies, does not force fluid into the catheter lumen during a connection or disconnection event. Also, the fluid connector assembly 100, unlike negative fluid displacement connector assemblies, does not allow fluid back into the catheter lumen during a connection or disconnection event. Accordingly, the fluid connector assembly 100 includes a neutral displacement connector assembly, without overlapping posts. In some embodiments, the fluid connector assembly 100 produces a positive fluid displacement during a connection or disconnection event. In some embodiments, the fluid connector assembly 100 produces a positive fluid displacement of less than 0.01 mL during a connection or disconnection event.

Figure 6A:
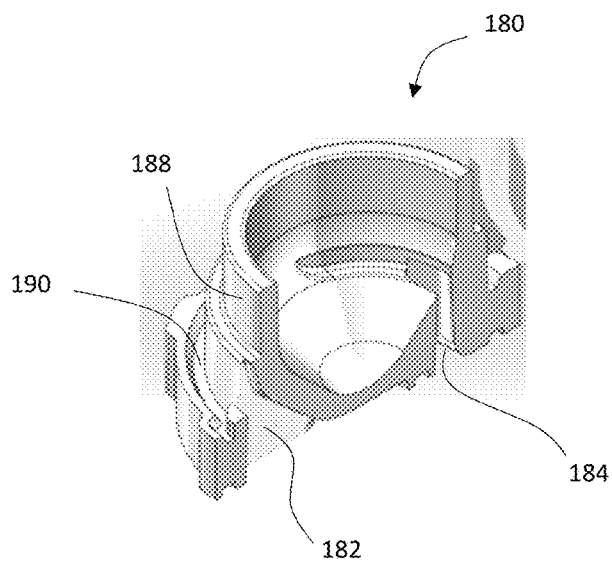
FIG. 6A illustrates a partial cross-sectional view of an insert, in accordance with aspects of the present disclosure.
Figure 6B:
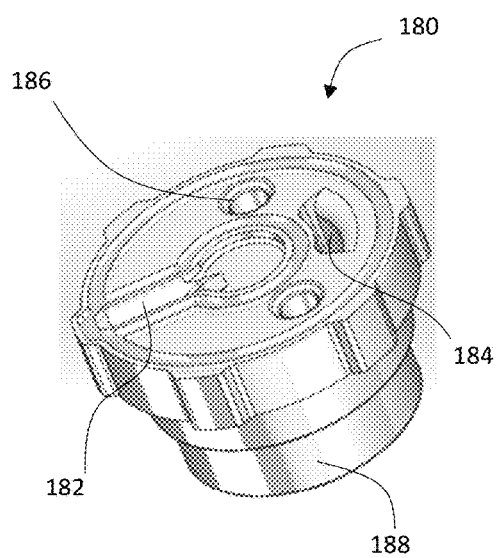
FIG. 6B illustrates a bottom perspective view of an insert, in accordance with aspects of the present disclosure.

FIGS. 6A and 6B illustrate the insert 180. FIG. 6A illustrates a partial cross-sectional view of the insert 180. In some embodiments, the insert is a generally cylindrical shape. In some embodiments, the insert 180 includes two apertures, a fluid channel 182 and an air channel 184. In some embodiments, the insert 180 may include only a fluid channel 182. The insert 180 may include a rim 188 around which the inner surface 130 of the compressible member 122 is fitted. When the connector 106 is coupled to the housing 102, the gate 132 moves as the compressible member 122 is deformed, moving the inner surface 130 and causing the inner surface 130 to cover the rim 188. The insert 180 further includes a trough 190 designed to collect the fluid and direct the fluid into the fluid channel 182. The trough 190 may extend circumferentially around the insert 180, or in some embodiments may only extend partially around the insert 180. The fluid channel 182, in accordance with aspects of the present disclosure, directs the fluid from the internal volume 124 of the housing 102 into the opening 116 of the connector 104. The air channel 184 supplies air into the internal volume 124 to facilitate the fluid flow through the fluid connector assembly. As shown in FIG. 6B, the side of the insert 180 that interfaces with the connector 104 includes a depression 186 to ensure proper alignment with the connector 104. In some embodiments, the insert 180 may include two or more depressions 186.

Figure 7:
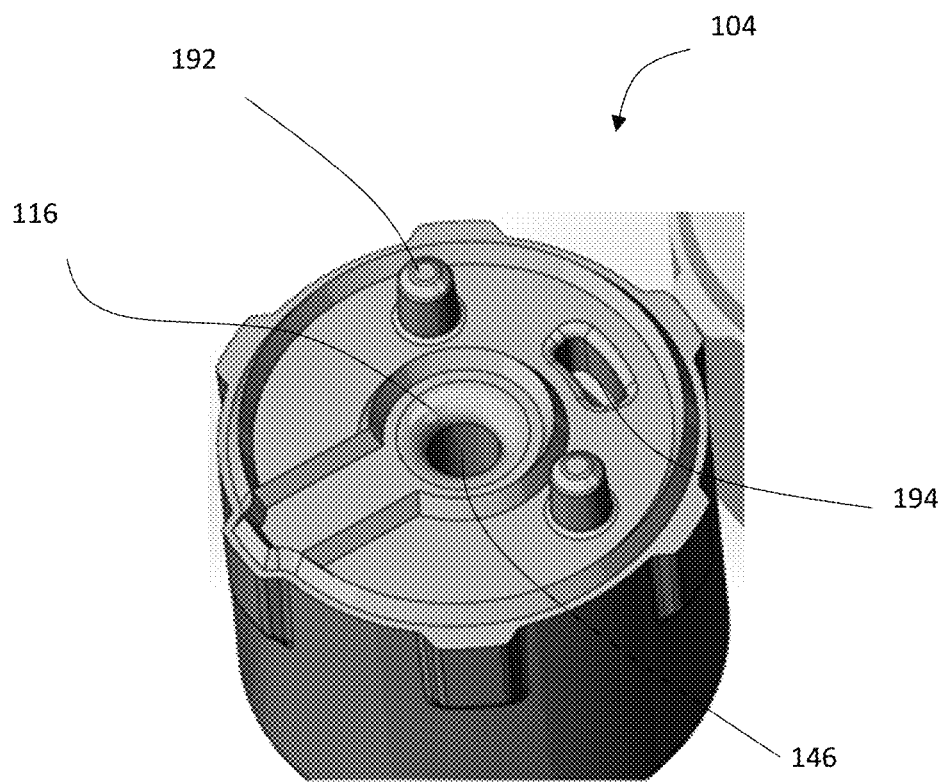
FIG. 7 illustrates a perspective view of a first connector, in accordance with aspects of the present disclosure.

FIG. 7 illustrates the connector 104 in accordance with aspects of the present disclosure. In some embodiments, connector 104 includes two apertures, the channel 146 for directing the fluid and an air channel 194. In some embodiments, the connector 104 may include only the channel 146. The side of the connector 104 that interfaces with the insert 180 may include a protrusion 192 to ensure proper alignment with the insert 180. In some embodiments, the connector 104 may include two or more protrusions 192.

Figure 8:
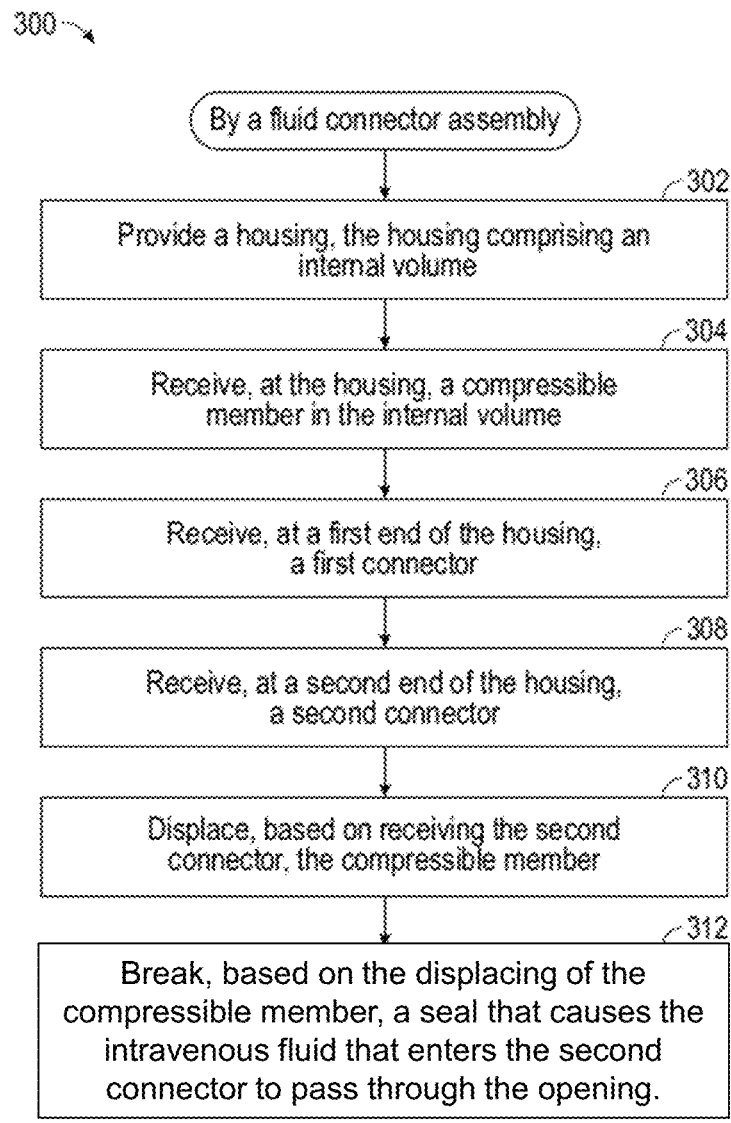
FIG. 8 illustrates a method for regulating an intravenous fluid, in accordance with aspects of the present disclosure

FIG. 8 illustrates a flowchart 300 showing a method for regulating an intravenous fluid, in accordance with aspects of the present disclosure. Fluid connector assemblies shown or described herein are capable of carrying out the steps of the method shown in the flowchart 300. In this regard, fluid connector assemblies with neutral fluid displacement may carry the steps of the method shown in the flowchart 300.

In step 302, a housing is provided. The housing may act as a central body for the fluid connector assembly. The housing may include an internal volume designed to receive, or at least partially receive, one or more components of the fluid connector assembly.

In step 304, a compressible member is received at the housing. Further, the compressible member is received in the internal volume of the housing. Further, the compressible member may elastically compress based on an external force and return to its original shape after the external force is removed.

In step 306, a first connector is received at a first end of the housing. The first connector may include a post and an opening formed in the post. The post, including the opening of the post, can be coupled to an insert and inserted into the housing, the insert being in contact with the compressible member. Also, the post of the first connector may form a fluid outlet for the fluid connector assembly.

In step 308, a second connector is received at a second end of the housing. The second connector may include a post that engages the compressible member. Also, the post of the second connector may include an opening that forms a fluid inlet for the fluid connector assembly.

In step 310, the compressible member is displaced based on receiving the second connector. The displacement of the compressible member may include a compression that causes a dimension (e.g., length) of the compressible member to reduce. However, based on the elastic features of the compressible member, the compressible member may return to its original size and shape when the second connector no longer engages the compressible member.

In step 312, a seal is broken based on the displacing of the compressible member. The seal breaking causes the intravenous fluid entering the second connector to pass through the opening of the post of the first connector. Further, the seal promotes neutral fluid displacement by limiting or preventing blood and/or other fluids from entering a catheter lumen when a connection or disconnection with the fluid connector assembly occurs.

Also, based on the location of the posts of the first and second connectors within the housing, the posts do not overlap each other. Put another way, the post of the first connector ("first post") does not enter the post of the second connector ("second post"), and the second post does not surround the first post. In this regard, a gap, located along a longitudinal axis of the first and second posts, provides a separation between the first and second posts, thus minimizing the likelihood of contact between the posts that can cause damage to at least one of the first and second posts.

The features of the present disclosure provide a fluid connector assembly with a compressible member that can be displaced to form a fluid pathway therebetween. When a first and a second connector are coupled together with a housing that carries the compressible member, the compressible member can compress and allow fluid flow, while also providing multiple seals to prevent unwanted fluid leakage. However, if a connector that displaces the compressible member is removed, whether unintentionally or intentionally, the fluid pathway the fluid connector assembly closes or is obstructed to prevent fluid loss therefrom, as the compressible member returns to its uncompressed state and closes off the fluid pathway. The features of the present disclosure also provide that upon separation of the first and second connectors, any of the first and second connectors can be cleaned and disinfected, and the first and second connectors can be once again coupled together to cause the compressible member to form a fluid pathway therebetween.

Illustration of Subject Technology as Clauses

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1, clause 8 or clause 15. The other clauses can be presented in a similar manner.

Clause 1. A fluid connector assembly comprising a housing comprising a first end in fluid communication with a second end through a cavity, a compressible member disposed within the housing, the compressible member comprising: at least one sealing element; and a gate, a first connector configured to couple to the housing at the first end, the first connector configured to deliver a fluid through the housing; and a second connector configured to couple to the housing at the second end, the second connector configured to receive a fluid from the housing.

Clause 2. The fluid connector assembly of Clause 1, wherein the second end of the housing comprises: a first path configured to direct the fluid into the second connector, and a second path configured to intake air.

Clause 3. The fluid connector assembly of Clause 2, wherein the second connector includes an ambient air aperture in fluid communication with the second path.

Clause 4. The fluid connector assembly of Clause 3, wherein the second connector is configured to provide air to the cavity when the first connector is coupled to the first end of the housing.

Clause 5. The fluid connector assembly of Clause 4, wherein the second connector includes at least one protrusion configured to align with at least one depression of the second end of the housing.

Clause 6. The fluid connector assembly of Clause 1, wherein the compressible member is configured to deform substantially to a first side of the cavity in a compressed configuration Clause 7. The fluid connector assembly of Clause 6, wherein the gate is located on the first side of the cavity.

Clause 8. A fluid connector assembly of Clause 7, wherein the gate is configured to translate from a second position when the compressible member is in the compressed configuration.

Clause 9. The fluid connector assembly of Clause 8, wherein the gate is configured to allow the fluid to travel to the second end of the housing into the second connector when the gate is in the second position.

Clause 10. The fluid connector assembly of Clause 1, wherein the compressible member further comprises a first portion and a second portion separated by the gate.

Clause 11. The fluid connector assembly of Clause 10, wherein the first portion extends from the gate toward the first end of the housing, and the second portion extends from the gate toward the second end of the housing.

Clause 12. The fluid connector assembly of Clause 11, wherein the first portion is configured to experience more deformation than the second portion when the first connector is coupled to the first end of the housing.

Clause 13. The fluid connector assembly of Clause 1, wherein the at least one sealing element is configured to extend radially within the cavity of the housing.

Clause 14. The fluid connector assembly of claim 13, wherein the at least one sealing element comprises a primary seal and a secondary seal.

Clause 15. The fluid connector assembly of claim 14, wherein the secondary seal is located proximate the first end of the housing and the primary seal is located in the cavity of the housing between the first end and the second end.

Clause 16. The fluid connector assembly of Clause 1, wherein the compressible member is configured to deform from an expanded configuration to a compressed configuration when the first connector is coupled to the housing.

Clause 17. The fluid connector assembly of Clause 16, wherein the at least one sealing element is configured to prevent fluid communication between the first end and the second end through the gate when the compressible member is in the expanded configuration.

Clause 18. The fluid connector assembly of Clause 17, wherein the at least one sealing element is configured to allow fluid communication between the first end and the second end through the gate when the compressible member is in the compressed configuration.

Clause 19. A fluid connector assembly comprising: a housing comprising a first end in fluid communication with a second end through a cavity, a compressible member disposed within the housing, the compressible member comprising: at least one sealing element; and a gate, a first connector configured to couple to the housing at the first end, the first connector configured to deliver a fluid through the housing; and a second connector configured to couple to the housing at the second end, the second connector configured to receive a fluid from the housing; wherein the compressible member is configured to deform from an expanded configuration to a compressed configuration when the first connector is coupled to the housing; and wherein the compressible member is configured to deform substantially to a first side of the cavity in the compressed configuration.

Clause 20. The fluid connector assembly of Clause 19, wherein the gate is configured to permit flow of fluid between the first end and second end past the gate when the compressible member is in the compressed configuration.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A fluid connector assembly comprising:
  a housing comprising a first end in fluid communication with a second end through a cavity,
  a compressible member disposed within the housing, the compressible member comprising:
    at least one sealing element; and
    a gate moveable relative to the housing, the gate configured to selectively control the flow of a fluid between the first end and the second end of the housing, a first connector configured to couple to the housing at the second end, the first connector configured to receive the fluid from the housing; and a second connector configured to couple to the housing at the first end, the second connector configured to deliver the fluid to the housing, wherein the compressible member is configured to deform radially toward a first side of the cavity when the second connector is coupled to the housing, and wherein the gate is configured to deform substantially toward the first side of the cavity when the second connector is coupled to the housing.

2. The fluid connector assembly of claim 1, wherein the compressible member is configured to deform from an expanded configuration to a compressed configuration when the second connector is coupled to the housing.

3. The fluid connector assembly of claim 2, wherein the at least one sealing element is configured to prevent fluid communication between the first end and the second end when the compressible member is in the expanded configuration.

4. The fluid connector assembly of claim 3, wherein the at least one sealing element is configured to allow fluid communication between the first end and the second end when the compressible member is in the compressed configuration.

5. The fluid connector assembly of claim 1, wherein the second end of the housing further includes an insert, the insert comprising:
 a first path configured to direct the fluid into the first connector, and
 a second path configured to deliver air to the cavity.

6. The fluid connector assembly of claim 5, wherein the first connector includes an air aperture in fluid communication with the second path.

7. The fluid connector assembly of claim 6, wherein the first connector is configured to provide air to the cavity.

8. The fluid connector assembly of claim 7, wherein the first connector includes at least one protrusion configured to align with at least one depression of the insert.

9. The fluid connector assembly of claim 1, wherein the compressible member further comprises a first portion and a second portion separated by the gate.

10. The fluid connector assembly of claim 9, wherein the first portion extends from the gate toward the first end of the housing and the second portion extends from the gate toward the second end of the housing.

11. The fluid connector assembly of claim 10, wherein the first portion is configured to experience more deformation than the second portion when the second connector is coupled to the housing.

12. The fluid connector assembly of claim 1, wherein the at least one sealing element is configured to extend circumferentially within the cavity of the housing.

13. The fluid connector assembly of claim 12, wherein the at least one sealing element comprises a primary seal and a secondary seal.

14. The fluid connector assembly of claim 13, wherein the secondary seal is located proximate the first end of the housing and the primary seal is located between the secondary seal and the gate.

15. The fluid connector assembly of claim 1, wherein at least a portion of the gate is configured to translate from a first position where the fluid is prevented from flowing between the first end and the second end to a second position where the fluid is allowed to flow between the first end and the second end when the second connector is coupled to the housing.

16. The fluid connector assembly of claim 1, wherein the compressible member is configured to deform axially toward the second end when the second connector is coupled to the housing.

17. A fluid connector assembly comprising:
 a housing comprising a first end in fluid communication with a second end through a cavity,
 a compressible member disposed within the housing, the compressible member comprising:
  at least one sealing element; and
  a gate moveable relative to the housing, the gate configured to selectively control the flow of a fluid between the first end and the second end of the housing,
 a first connector configured to couple to the housing at the second end, the first connector configured to receive the fluid from the housing; and
 a second connector configured to couple to the housing at the first end, the second connector configured to deliver the fluid to the housing;
 wherein the compressible member is configured to deform from an expanded configuration to a compressed configuration when the second connector is coupled to the housing,
 wherein the compressible member is configured to deform radially toward a first side of the cavity when the second connector is coupled to the housing,
 wherein at least a portion of the gate is configured to translate from a first position to a second position when the second connector is coupled to the housing,
 wherein the compressible member is configured to deform substantially to the first side of the cavity in the compressed configuration, and
 wherein the gate is configured to deform substantially toward the first side of the cavity when the second connector is coupled to the housing.

18. The fluid connector assembly of claim 17, wherein the gate is configured to permit flow of fluid between the first end and second end past the gate when the compressible member is in the compressed configuration.

* * * * *